United States Patent
Wu et al.

(10) Patent No.: US 7,512,435 B2
(45) Date of Patent: Mar. 31, 2009

(54) DELAY-COMPENSATED CALCULATION OF TISSUE BLOOD FLOW

(75) Inventors: Ona Wu, Cambridge, MA (US); Gregory Sorensen, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 6 days.

(21) Appl. No.: 10/558,343

(22) PCT Filed: Jun. 2, 2004

(86) PCT No.: PCT/US2004/017129
§ 371 (c)(1), (2), (4) Date: Jan. 12, 2007

(87) PCT Pub. No.: WO2005/009204
PCT Pub. Date: Feb. 3, 2005

(65) Prior Publication Data
US 2007/0112264 A1    May 17, 2007

Related U.S. Application Data (60) Provisional application No. 60/475,384, filed on Jun. 2, 2003.

(51) Int. Cl.
*A61B 6/00* (2006.01)
*A61B 5/06* (2006.01)

(52) U.S. Cl. .................. 600/431; 600/410; 600/419; 600/420; 378/4

(58) Field of Classification Search .......... 600/419, 600/420, 410, 431; 378/4
See application file for complete search history.

(56) References Cited

U.S. PATENT DOCUMENTS

| | | | |
|---|---|---|---|
| 5,287,273 A * | 2/1994 | Kupfer et al. ............... 600/431 |
| 5,576,548 A | 11/1996 | Clarke et al. |
| 5,867,416 A | 2/1999 | Feldmann et al. |
| 6,370,279 B1 * | 4/2002 | Paik ........................... 382/268 |
| 6,389,304 B1 | 5/2002 | van den Brink et al. |
| 6,402,689 B1 | 6/2002 | Scarantino et al. |
| 6,542,769 B2 * | 4/2003 | Schwamm et al. .......... 600/420 |
| 6,546,275 B2 | 4/2003 | Carroll |
| 6,803,954 B1 * | 10/2004 | Hong et al. .................. 348/260 |
| 7,069,068 B1 * | 6/2006 | Ostergaard ................... 600/420 |
| 2002/0111550 A1 * | 8/2002 | Schwamm et al. .......... 600/419 |
| 2003/0045791 A1 * | 3/2003 | Carroll ....................... 600/419 |
| 2003/0076988 A1 * | 4/2003 | Liang et al. ................. 382/131 |
| 2004/0044281 A1 * | 3/2004 | Jesberger et al. ............ 600/419 |
| 2004/0084624 A1 * | 5/2004 | Meng et al. ................. 250/363.1 |
| 2004/0189297 A1 * | 9/2004 | Bock et al. .................. 324/307 |
| 2004/0249265 A1 * | 12/2004 | Fuchs et al. ................. 600/419 |

* cited by examiner

*Primary Examiner*—Long V Le
*Assistant Examiner*—Helene Bor (57) ABSTRACT

Methods for computing perfusion parameters are described. The methods are typically used to analyze magnetic resonance (MR) and other image data and to calculate tissue perfusion parameters such as blood flow in the brain or in tissues in other organs such as the heart. The methods employ a block-circulant matrix for deconvolving the perfusion parameters from the image data.

14 Claims, 9 Drawing Sheets

DELAY-COMPENSATED CALCULATION OF TISSUE BLOOD FLOW

CROSS-REFERENCE TO RELATED APPLICATIONS

This application is a national phase application under 35 U.S.C. § 371 of PCT International Application No. PCT/US2004/017129, filed Jun. 2, 2004, which claims the benefit of U.S. Provisional Patent Application Ser. No. 60/475,384, filed Jun. 2, 2003. The contents of these prior applications are incorporated by reference in their entirety.

STATEMENT AS TO FEDERALLY SPONSORED RESEARCH

This invention was made with Government support under 5 R01 NS38477, 5 R01 HL39810, and 5P41 RR14075, awarded by the National Institutes of Health. The Government has certain rights in the invention.

TECHNICAL FIELD

The invention relates to methods for performing perfusion measurements in tissues such as in the brain or heart.

BACKGROUND

Ischemia is a reduction of blood flow, e.g., in the brain, that can result in metabolic impairment and neurological dysfunction. Ischemia in the brain typically results in a stroke. One of the research goals in stroke imaging is to identify the imaging correlate to the ischemic penumbra, tissue that is oligemic, i.e., has a lower blood volume, but is still viable. It is this tissue that has been speculated to maximally benefit from therapeutic intervention. An accurate in vivo measure of cerebral blood flow (CBF) may help guide therapeutic strategies on an individual patient basis.

Perfusion weighted SEW) magnetic resonance (MR) imaging, in which one tracks the passage of a bolus of a contrast agent, has been demonstrated to be useful for detecting tissue at risk of infarction. For example, see "Magnetic resonance imaging of acute stroke" by Baird et al., *J. Cereb. Blood Flow Metab.*, 18:583-609 (1998). In general, contrast agent-based CBF maps are estimated by deconvolving tissue concentration curves with an arterial input function (AIF). This technique has been shown to be both sensitive to delay and dispersion between the AIF and the tissue concentration curve. For example, refer to "Modeling cerebral blood flow and flow heterogeneity from magnetic resonance residue data," by Østergaard et al. in *J. Cereb. Blood Flow Metab.*, 19:690-699 (1999) and "Delay and dispersion effects in dynamic susceptibility contrast MRI: simulations using singular value decomposition," by Calamante et al. in Magn. Reson. Med., 44:466-473 (2000). Because perfusion maps depend on the selection of the AIF, determination of a threshold of irreversible ischemia is complicated and makes identification of tissue at risk of infarction sensitive to user variability. Furthermore, such artifacts may negatively affect patient management. For example, a vascular territory whose feeding artery is occluded will suffer delayed flow as well as reduced flow. However, even if the territory has sufficient collateral flow, the tissue may have an estimated CBF that is artificially oligemic due to these technical limitations.

SUMMARY

The invention is based, in part, on the discovery of a method to measure tissue blood flow, e.g., cerebral blood flow (CBF), which is less sensitive than prior methods to delays in bolus arrival between an arterial input function (AIF) and the region of interest. Such delay insensitivity is achieved by performing deconvolution with a block-circulant matrix and optionally by using local, rather than global, regularization.

In general, the invention features methods of determining a blood flow parameter in a specific tissue in a subject by obtaining image data of the specific tissue generated by the administration of a contrast agent to the specific tissue through an artery; determining an arterial input function (AIF) from the image data; generating a block-circulant matrix using the AIF; calculating a residue function by deconvolution using the block-circulant matrix; and determining a blood flow parameter in the specific tissue from the residue function.

One embodiment of these methods is a method of determining a cerebral blood flow parameter in a subject by determining an arterial input function (AIF) from a magnetic resonance image of a contrast agent in subject's brain; calculating a residue function from the (AIF) using singular value decomposition with a block-circulant matrix; and determining a cerebral blood flow parameter using the residue function. This method can further include repeatedly deconvolving the residue function, wherein each deconvolution is performed using a different threshold; calculating an oscillation index for each deconvolved residue function; and selecting the residue function from the repeatedly calculated residue functions such that the residue function has an oscillation index below a set level.

In these methods, the image data can be one or more (e.g., a set of) magnetic resonance (MR), positron emission tomography (ET), or computed tomography (CT) images. The contrast agent can be a dye or a bolus of oxygen. The AIF can be determined by averaging signal changes in pixels selected from regions of the image near a large blood vessel. In certain embodiments, the block-circulant matrix D can be decomposed by D=U·S·V, where U and V are orthogonal matrices and S is a non-negative square diagonal matrix.

In various embodiments of these methods, the blood flow parameter can be relative cerebral blood flow (rCBF), relative cerebral blood volume (rCBV), or mean transit time MTT) of the contrast agent in the tissue. rCBF can be determined by calculating the maximum value of the residue function. rCBV can be determined by calculating:

$$rCBV = \frac{\int_0^\infty C_{VOI}(t)dt}{\int_0^\infty C_a(t)dt},$$

wherein $C_{VOI}(t)$ is contrast agent concentration over time, and $C_a(t)$ is the concentration of the contrast agent flowing into the specific tissue. The MTT can be determined by calculating:

$$MTT = \frac{rCBV}{rCBF}.$$

In certain embodiments, the residue function is deconvolved using singular value decomposition (SVD) of the block-circulant matrix. In general, the new methods can be used, for example, to identify tissue at risk of infarction in a subject, e.g., in the brain of a subject.

In another aspect, the invention features machine-readable storage media having encoded thereon a software program that causes a processor associated with an imaging device to obtain image data of a tissue generated by the administration of a contrast agent to the tissue through an artery, compute an arterial input function (AIF) from the image data; generate a block-circulant matrix using the AIF; calculate a residue function by deconvolution using the block-circulant matrix; and calculate a tissue blood flow parameter in the tissue from the residue function. The software can further cause the processor to display the tissue blood flow parameter, and the tissue blood flow parameter can be relative cerebral blood volume (rCBV), relative cerebral blood volume (rCBV), or mean transit time (MTT) of the contrast agent. These are calculated as described herein.

In another aspect, the invention includes systems for imaging tissue that include an imaging device; a processor associated with the imaging device; a memory coupled to the processor, the memory containing software that, when executed, causes the processor to: (i) obtain image data of the tissue generated by the administration of a contrast agent to the tissue through an artery; (ii) compute an arterial input function (AIF) from the image data; (iii) generate a block-circulant matrix using the AIF; (iv) calculate a residue function by deconvolution using the block-circulant matrix; and (v) calculate a blood flow parameter in the tissue from the residue function. The system also typically includes (d) an output device for displaying the blood flow parameter, and an input device for entering data or instructions.

In these systems, the imaging device can be a magnetic resonance (MR), positron emission tomography (PET), or computed tomography (CT) imaging device.

For all of the new methods, software, and systems, the subject can be a human or animal, e.g., a mammal, such as a domesticated mammal, such as a dog, cat, horse, cow, goat, or pig. The new methods also work for other animals that have circulatory systems.

In certain embodiments of the methods, software, and systems, the residue function is calculated by deconvolving the tissue concentration curve with the AIF using singular value decomposition (SVD) of the block-circulant matrix, where the block-circulant matrix D can be decomposed by $D = U \cdot S \cdot V$, where U and V are orthogonal matrices, and S is a non-negative square diagonal matrix.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 3A to 3D are a series of graphs showing a comparison of performances of sSVD (standard SVD), oSVD (SVD with minimization of oscillation index) and cSVD (circular SVD) in estimating flow for SNR=100 (FIG. 3A) and 20 (FIG. 3B).

FIGS. 5A-D are a series of graphs that each show a comparison of performances of sSVD, oSVD, and cSVD in estimating tracer arrival time differences for SNR=100 (5A) and 20 (5B) with TR=1 second, and CBV=4% and underlying monoexponential R(t). $\overline{ED}(F)$ and $\sigma_{ED}(F)$ plotted as a function of F demonstrate that all techniques produce poor estimates at low flow. sSVD produces less $\overline{ED}(F)$ at low flow rates and SNR than oSVD and cSVD. FIGS. 5C and 5D show estimated shifts (D') as a function of true shift (D) at F=60 ml/100 g/min, and demonstrate that for D≧0, sSVD performs comparably to cSVD and OSVD at SNR=100, and overestimates large shifts to a greater extent at SNR=20.

FIGS. 6A to 6I are a series of representations of MM images that show the performances of sSVD and oSVD techniques in a patient (Patient 1) who had an ICA stenosis in which there were large sCBF and sMTT abnormalities (arrowheads) that do not infarct and minimal oCBF and oMTT lesions (arrows). FIG. 6B shows the sCBF, FIG. 6C shows the sMTT, FIG. 6F shows the oCBF, FIG. 6G the oMTT.

FIGS. 7A to 7I are a series of MRI images (Patient 2) that show that both sSVD and oSVD can detect regions of tissue at risk of infarction that is initially normal in the DWI. FIG. 7A shows a normal DWI. FIG. 7C shows sMTT, FIG. 7D the sDelay map, FIG. 7E the CBV, FIG. 7F the oCBF (arrow shows lesion), FIG. 7J shows a 22-day follow-up FLAIR, which shows the infarct lesion matches with abnormalities on both sSVD and oSVD perfusion maps (arrows).

FIGS. 8A to 8I are a series of MRI images (Patient 3), that show a mismatch in DWI and PWI lesion volumes when using sSVD and no mismatch when using oSVD (arrows show lesion). FIG. 8E shows the CBV. FIG. 8J shows a 4-month follow-up FLAIR, which shows an infarct that is well matched with the patient's acute DWI, CBV, oCBF, and oMTT studies (arrows).

FIGS. 9A to 9P are a series of MRI images that show a comparison of sensitivity of sSVD and oSVD to AIF selection in Patient 4. Lesions on initial (9A) DWI and (9B) CBV studies (small arrows) extend into larger infarct volume shown on (9C) 6-day follow-up FLAIR. FIGS. 9D (sCBF), 9E (sMTT), 9F (sDelay), 9G (oCBF), 9H (oMTT), and 9I (oDelay maps) were imaged using AIF1. Regions darker than background on the (9I) oDelay map represent negative values (small arrow). FIGS. 9K (sCBF), 9L (sMTT), 9M (sDelay), 9N (oCBF), 9O (oMTT), and 9P (oDelay map) were imaged using AIF2. Regions of hyperperfusion (arrows) or hypoperfusion (arrowheads) depend on AIF selection for sSVD, but not for oSVD as best seen in FIGS. 9G and 9N.

DETAILED DESCRIPTION

The invention features new methods for performing perfusion measurements in the brain. The new methods improve cerebral blood flow estimates in two ways: (1) by performing deconvolution with a block-circulant matrix to reduce sensitivity to tracer arrival differences between the AIF and tissue signal, and (2) by using local, rather than global regularization. In the following text, we first describe a known method for performing perfusion measurements, and outline the general mathematical framework for deconvolution using standard singular value decomposition techniques (sSVD). The known method employs singular value decomposition (SVD) to deconvolve the blood flow data from measured magnetic resonance data, but this method is sensitive to certain types of delays. After the description of the prior art method, we describe the new methods. The new methods use a block-circulant deconvolution matrix method whose flow calculations are delay invariant.

Then, in the Examples, we evaluate the performance of the new methods as well as the existing deconvolution approach using SVD in terms of flow estimation errors as a function of tracer arrival differences using numerical simulations where CBF values are known. In addition, techniques for estimating tracer arrival differences with respect to the AIF are evaluated. The performances of the methods are also compared qualitatively on clinically acquired human PW MRI data. In particular, we examine two conditions that have been previously demonstrated to be problematic for SVD de-convolution—when there exists internal carotid artery (ICA) stenosis, and when the AIF regionally lags the tissue signal—as well as two acute stroke cases where initial perfusion lesion volumes calculated using standard techniques are greater than diffusion weighted imaging (DWI) lesion volumes.

Relationship Between MRI Data and Perfusion Models

First, the general method of measuring perfusion parameters using magnetic resonance imaging is described. Typically, the data for the perfusion measurements are obtained by recording a time series of images of the brain, while an injected bolus of contrast agent transits the brain. The contrast agents influence the MR signal and by tracking the time evolution of these changes in the brain images, perfusion parameters are extracted from the data.

Lanthanide chelate contrast agents produce changes in transverse relaxation time ($\Delta R_2$) proportional to their concentration in magnetic susceptibility MR imaging. During the passage of a bolus of a high magnetic susceptibility contrast agent, tissue surrounding the vessels produces a transient loss of signal due to the intravascular compartmentalization of the contrast agent. The relationship between image intensity and change in susceptibility $\Delta R_2$ (or $\Delta R_2^*$ in a gradient echo experiment) is given by.

$$S(t) = S_0 e^{-TE \cdot \Delta R_2} \quad [1]$$

where $S_0$ is the baseline MR image intensity prior to administration of contrast agent, $S(t)$ is signal as a function of time, and TE is the echo time of the acquisition. The contrast agent concentration over time, $C_{VOI}(t)$, is linearly related to $\Delta R_2$ as follows:

$$C_{VOI}(t) \propto \Delta R_2(t) = -\frac{1}{TE} \ln \frac{S(t)}{S_0}. \quad [2]$$

Figure 1:
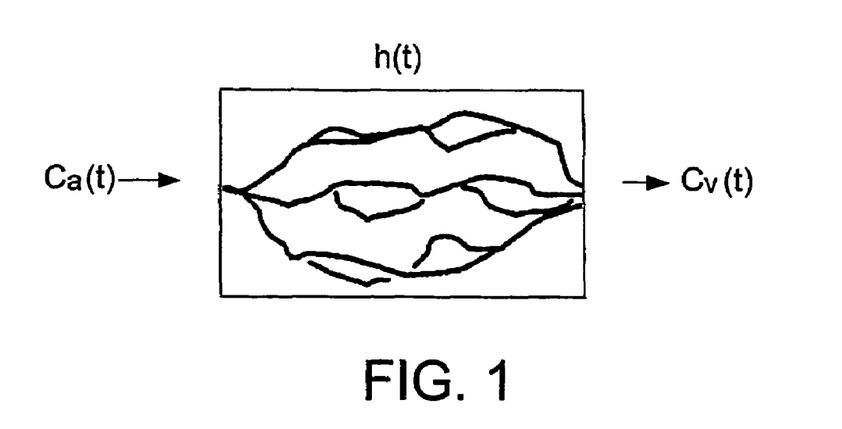
FIG. 1 is a simplified schematic model of the relationship between tracer influx and tracer outflux.

Traditional tracer kinetic models for intravascular agents can be extended to dynamic susceptibility contrast MRI data to calculate cerebral blood flow (CBF) and tracer mean transit time (MTT). Modeling the vascular bed as a fluid dynamic system consisting of a single in-flow and single out-flow with multiple capillary branches in between, the distribution of transit times can be characterized by a transfer function, h(t), as shown in FIG. 1 where $C_a(t)$ is the concentration flowing in, $C_v(t)$ the concentration flowing out, and h(t) has the following property:

$$\int_0^\infty h(t) dt = 1. \quad [3]$$

This relationship can be formulated as, $$C_v(t) = F_t C_a(t) \otimes h(t) \quad [4]$$

where $\otimes$ represents a linear convolution operator.

Furthermore, by defining the fraction of tracer remaining in the system, also known as the residue function, R(t) as $$R(t) = 1 - \int_0^t h(\tau) d\tau, \quad [5]$$

where $\tau$ is the time variable, the concentration of tracer remaining within the voxel of tissue is modeled as:

$$C_{VOI}(t) = F_t C_a(t) \otimes R(t) = F_t \int_0^t C_a(\tau) R(t-\tau) d\tau \quad [6]$$

where $C_a(t)$ is the concentration at the input artery (the arterial input function) and $F_t$ is the flow within the tissue system.

Analysis of MR Data by a Standard SVD Method

The standard SVD method for computing perfusion parameters uses the magnetic resonance based perfusion measurements described above. Assuming both $C_a(t)$ and $C_{VOI}(t)$ (See Eq. [2]) are extracted from the image data, then R(t) can then be estimated via deconvolution.

The SVD technique expresses Eq. [6] in discretized format:

$$c(t_j) = \Delta t F_t \sum_{i=0}^{j} C_a(t_i) R(t_j - t_i). \quad [7]$$

where $c(t_j)$ is tissue concentration as a function of time. By rewriting Eq. [7] into matrix notation, the deconvolution problem can be expressed as an inverse matrix problem:

$$\begin{pmatrix} c(t_0) \\ c(t_1) \\ \vdots \\ c(t_{N-1}) \end{pmatrix} = \Delta t \begin{pmatrix} C_a(t_0) & 0 & \cdots & 0 \\ C_a(t_1) & C_a(t_0) & \cdots & 0 \\ \vdots & \vdots & \ddots & \vdots \\ C_a(t_{N-1}) & C_a(t_{N-2}) & \cdots & C_a(t_0) \end{pmatrix} \cdot \begin{pmatrix} R(t_0) \\ R(t_1) \\ \vdots \\ R(t_{N-1}) \end{pmatrix} \cdot F_t. \quad [8]$$

Simplifying the above equation to:

$$c = F_t A \cdot b \quad [9]$$

where c is a vector whose elements are the discrete time points of the change in concentration of contrast agent in the tissue and A is the matrix in Eq. 8 scaled by $\Delta t$, one can solve for b, a vector whose elements are discrete time samples of R(t).

The measured AIF, $C_\alpha(t)$, can also be prefiltered to reduce noise contributions and compensate for quantization errors. Such filtering results in A with elements:

$$a_{ij} = \begin{cases} \Delta t (C_a(t_{i-j-1}) + 4 C_a(t_{i-j}) + C_a(t_{i-j+1})) & 0 \le j \le i \\ 0 & \text{otherwise} \end{cases}. \quad [10]$$

Since A may be close to singular, the inverse of A is calculated using SVD. A is decomposed to:

$$A = U \cdot S \cdot V \quad [11]$$

where U and V are orthogonal matrices, and S is a non-negative square diagonal matrix.

The inverse is then simply:

$$A^{-1} = V \cdot W \cdot U^T \quad [12]$$

where W=1/S along the diagonals, and zero elsewhere. In SVD, a user set tolerance threshold controls the stability of the inverse. Values of W corresponding to values where S is smaller than the preset tolerance threshold (usually a percentage of the maximum value of S) are set to zero to eliminate singular values and to produce a more stable result Typically, the threshold is set high enough to reduce the impact of noise on the inverse, yet the threshold is not so high that the information content of the inverse is eliminated.

Having computed the inverse with SVD, the residue function scaled by flow $F_t b$, can then be estimated by:

$$F_t b = V \cdot W \cdot U^T \cdot c. \quad [13]$$

From $F_t b$, which is the estimated, scaled R(t), relative cerebral blood flow (rCBF) is set equal to its maximum value, which often does not occur at the zero time point due to tracer arrival delay.

Other perfusion parameters are also found by processing the obtained data. For example, by integrating Eq. [2] with respect to time, relative cerebral blood volume (rCBV) can be obtained:

$$rCBV = \frac{\int_0^\infty C_{VOI}(t) \, dt}{\int_0^\infty C_a(t) \, dt} \quad [14]$$

assuming no recirculation or consumption of the contrast agent. Mean transit time (MTT) is calculated using the Central Volume Theorem:

$$MTT = \frac{rCBV}{rCBF}. \quad [15]$$

The above description examines the theory and analysis for one voxel of image data. Similar processing is typically done for all pixels of the image to provide spatially extended images. By computing such parameters for each voxel, maps of perfusion indices are calculated to assist in clinical diagnosis.

Delay Errors Using Standard SVD

Although the standard SVD method is often used to calculate perfusion parameters such as CBF, standard SVD can produce erroneous results when the AIF ($C_\alpha(t)$) lags the tissue signal ($C_{VOI}(t)$). Such a situation occurs naturally when the AIF is selected downstream from an occlusion. Therefore, with the existing technique, relative flows within an imaging session may not be accurate, because a shifted AIF may result in an overestimated CBF in some voxels and an underestimated CBF in other voxels. As a result, oligemic tissue may be incorrectly diagnosed as ischemic. This has implications in clinical settings where the mismatch between diffusion weighted images (DWI) and perfusion weighted images (PWI) may cause lesion volumes to be overestimated, resulting in greater amounts of tissue categorized as at risk of infarction than is truly at risk.

Perfusion Parameters using Circular Deconvolution

Figure 2:
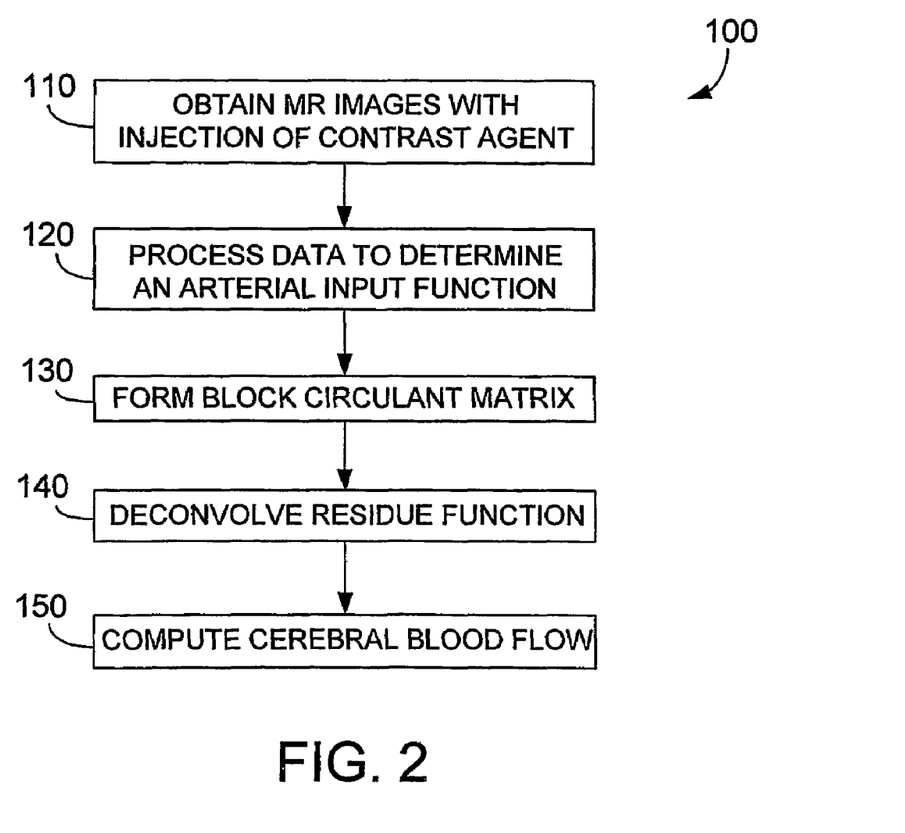
FIG. 2 is a flowchart outlining a method to calculate cerebral blood flow.

The new methods are less sensitive to timing shifts between the $C_v(t)$ and AIF than method described above. FIG. 2 outlines general method 100, which computes perfusion parameters by deconvolving the residue function by using a non-causal deconvolution technique. In the embodiments described below, the methods employ a block-circulant matrix in the SVD to deconvolve the residue function.

Step 110: Obtain Images with Injection of a Contrast Agent

Method 100 first obtains images, such as magnetic resonance (MR), computed tomography (CT), or positron emission tomography (PET) images, by monitoring the injection of a bolus of a contrast agent such as a dye or even a bolus of oxygen (Step 110). In some embodiments, method 100 acquires dynamic susceptibility contrast-weighted (DSC) MR images (DSC MRI) using either spin-echo (SE) or gradient recalled-echo (GRE) echo planar imaging (EPI) during the first pass of 0.1-0.2 mmol/kg of a gadolinium-based contrast agent injected 10 seconds after the start of imaging at a rate of 5 ml/s with the use an MR imaging-compatible power injector (Medrad, Pittsburgh, Pa.). Typically the bolus of contrast agent is followed by a comparable volume of normal saline injected at the same rate. Using such pulse sequences, datasets of 10-11 slices over 46 time points are typically obtained. The in-plane resolution of the images is typically 1.56×1.56 mm². Each slice is typically 6 mm thick with a 1 mm interslice gap. In embodiments that use spin echoes, typically the pulse sequences use TR=1500 ms and TE=75 ms. In embodiments that use gradient recalled echoes, typically the pulse sequences use TR=1499 ms and TE=50 ms.

CT perfusion images may be acquired in a manner similar to MRI if rapid scanning is performed before, during, and after the injection of a tracer. In CT, typical scanning could include single or multiple slices with repetition times of 1 to 2 seconds; the tracer could be an iodinated contrast agent, and the resolution overall would not be too dissimilar from that described for MRI (for example, 0.5 mm×0.5 mm×5 mm). A method using an arterial input function (with or without a venous input function) could also be used to reconstruct the CBF maps. In PET, the tracer can be oxygen-15 or other radiotracer, again with rapid imaging before, during, and after injection of the tracer. When using PET, the arterial input function could be measured directly from the heart or from other vessels.

Step 120: Process Data to Determine AIF

Having collected the data, method 100 includes processing the images to compute an arterial input function (Step 120). The arterial input function (AIF) is obtained by averaging the signal changes in pixels selected from regions near large cerebral vessels in the MR images that showed early large increases in $\Delta R_2$ after contrast injection (See Eq. [2]). The AIF cannot be measured directly in a large vessel, for example the middle cerebral artery (MCA), since the change in signal does not follow Eq. [2] due to large flow effects and dependence of signal change on orientation of the large vessel. Instead, the AIF is typically selected in voxels near the large vessel where the signal change has been demonstrated to follow Eq. [2]. Without knowledge of the absolute concentration of contrast agent passing through the vessels resulting in the measured AIF, a quantitative calculation of CBF in terms of ml/100 g/min is typically not possible. Instead, relative flow values are calculated, which differ from the absolute CBF by a scale factor. Typically, a single AIF is used for deconvolving Eq. [6] to calculate relative CBF for all of the voxels in the brain.

Step 130: Form Block-Circulant Matrix

Having determined the AIF, method 100 uses the AIF to form the block-circulant deconvolution matrix D (Step 130). Implicit in the standard SVD technique described herein is the assumption of causality as seen in the constraints in Eqs. [8]-[10] that $a_{ij}=0$ for $j>i$. This assumption is violated when $C_a(t)$ lags $C_v(t)$ and, as described above, occurs naturally.

Instead of linear deconvolution, the present method uses circular deconvolution. Circular convolution is equivalent to linear convolution with time aliasing. If one assumes that the signal was sampled for a sufficient duration such that $C_v(t)$ is not truncated, then time aliasing will not be a consideration. Furthermore, by zero-padding the N-point time series $C_a(t)$ and $C_v(t)$ to length L, where $L \geq 2N-1$, time aliasing is avoided. Therefore, replacing matrix A in Eq. [8] and Eq. [9] with a block-circulant matrix, D:

$$D = \begin{pmatrix} C_a(t_0) & C_a(t_{N-1}) & \cdots & C_a(t_1) \\ C_a(t_1) & C_a(t_0) & \cdots & C_a(t_2) \\ \vdots & \vdots & \ddots & \vdots \\ C_a(t_{N-1}) & C_a(t_{N-2}) & \cdots & C_a(t_0) \end{pmatrix} \quad [16]$$

Eq. [9] can be reformulated as:

$$g = F_t D \cdot f, \quad [17]$$

where g is the zero-padded c and f is the residue function scaled by $F_t$ to be determined.

Step 140: Deconvolve Residue Function using SVD with the Block-Circulant Matrix

Having computed the block-circulant matrix D, the method calculates the residue function by deconvolution using SVD (Step 140). The block-circulant matrix D is decomposed by:

$$D = U \cdot S \cdot V \quad [18]$$

where U and V are orthogonal matrices and S is a non-negative square diagonal matrix. The inverse is then simply:

$$D^{-1} = V \cdot W \cdot U^T \quad [19]$$

where W=1/S along the diagonals, and zero elsewhere. Values of W corresponding to values where S is smaller than a preset tolerance threshold (usually a percentage of the maximum value of S) are set to zero to eliminate singular values and to produce a more stable result. The residue function scaled by flow, $F_t b$, can then be calculated by:

$$F_t b = V \cdot W \cdot U^T \cdot c. \quad [20]$$

As described above, in SVD there exists a user set tolerance threshold. The threshold is set high enough to reduce the impact of noise on the inverse, yet the threshold is not so high that the information content of the inverse is erased. Typical clinical thresholds range between 10-20% of the maximum value of S, depending on the SNR of the acquired data. See, e.g., Liu et al., Magn. Reson. Med., 42:167-172 (1999).

In some embodiments, the SVD threshold itself is not user defined. Instead the user defines a maximum allowable oscillation index. When using circular deconvolution, due to the discontinuity between t=0 and t=L, leakage frequencies may be amplified giving rise to spurious oscillations that can dominate the deconvolved signal. Increasing $P_{SVD}$ reduces these oscillations. Using a modified oscillation index (O) from that described in "A deconvolution method for evaluating indicator-dilution curves" by Gobbel et. al., in *Phys Med-Biol.*, 39:1833-1854, (1994):

$$O = \frac{1}{L} \frac{1}{f_{max}} \left( \sum_{k=2}^{L-1} |f(k) - 2f(k-1) + f(k-2)| \right) \quad [21]$$

where $f$ is a scaled, estimated residue function, $f_{max}$ is the maximum amplitude of $f$, and L is the number of sample points, $P_{SVD}$ can be varied until the estimated residue function's oscillation index falls below a user-specified value (OI) and CBF set to $f_{max}$ at that instance.

Step 150: Compute Tissue Blood Flow

Using the computed data, the method computes the perfusion parameters (Step 150). For example, when measuring cerebral blood flow, rCBF is set equal to the maximum value of $F_t b$, which often does not occur at the zero time point due to tracer arrival delay. By integrating Eq. [2] with respect to time, relative cerebral blood volume (rCBV) can be obtained according to Eq. [14] assuming that there is no recirculation or consumption of the contrast agent. MTT can then be calculated using Eq. [15].

Implementation

In some embodiments, the steps described above are implemented in computer programs using standard programming techniques. Such programs are designed to execute on programmable computers each comprising an electronic processor, a data storage system (including memory and/or storage elements), at least one input device, and at least one output device, such as a display or printer. In some embodiments, the program code is applied to control the acquisition of the image data, such as MRI data, using a pulse sequence stored in the software. In other embodiments, the code is applied directly to acquired data (e.g., MRI data from the spectrometer) to perform the functions described herein and generate output information (e.g. cerebral blood flow, mean transit time, or cerebral blood volume), which is applied to one or more output devices. In yet other embodiments, the program code is applied to acquisition of the data by controlling a MR spectrometer and to the subsequent analysis described herein. Each such computer program can be implemented in a high-level procedural or object-oriented programming language, or an assembly or machine language. Furthermore, the language can be a compiled or interpreted language. Each such computer program can be stored on a computer readable (machine-readable) storage medium (e.g., CD ROM or magnetic diskette) that when read by a computer can cause the processor in the computer to perform the analysis described herein.

The software can be manufactured and/or sold, e.g., by MRI manufacturers, either as part of the original software supplied to new MRI or other imaging device, or as a later add-on "upgrade" to existing imaging devices. The software can also be made and/or sold by independent software manufacturers directly to users of such MRI or other imaging devices.

Figure 10:
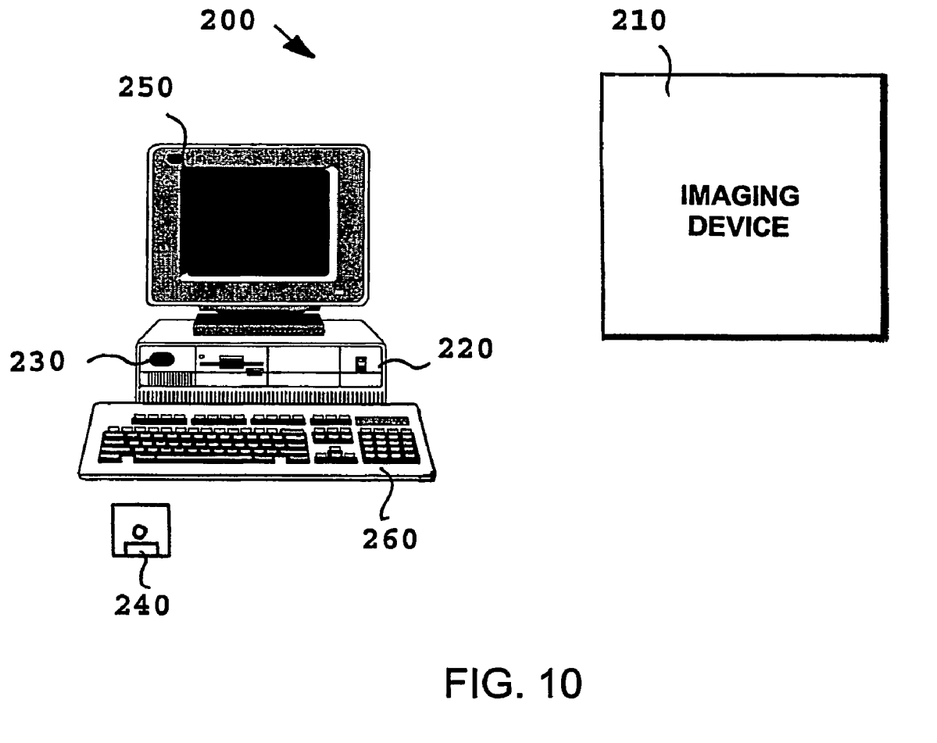
FIG. 10 is a schematic diagram of an imaging system that can incorporate the new methods embodied in software.

The software can be used in imaging systems, that are standard, but for the new software. For example, as shown in FIG. 10, the imaging system 200 can include an imaging device 210, such as an M, PET, or CT imaging device; a processor 220, such as a PC or microprocessor, associated with the imaging device; and a memory 230 coupled to the processor that contains the new software, or reads the software from a computer-readable storage medium 240. The memory contains the new software that, when executed, causes the processor to: obtain image data of the tissue generated by the administration of a contrast agent to the tissue through an artery, compute an arterial input function (AIF) from the image data; generate a block-circulant matrix using the AIF; calculate a residue function by deconvolution using the block-circulant matrix; and calculate a blood flow parameter in the tissue from the residue function. The system can also include an output device 250 for displaying the blood flow parameter, such as a monitor, e.g., CRT, or printer. The system can also include an input device 260, such as a keyboard or mouse, for providing data or instructions to the system.

EXAMPLES

The invention is further described in the following examples, which do not limit the scope of the invention described in the claims.

The methods described herein were applied in various settings and the resulting data was compared. First, simulated results are described. The simulations are followed by a number of examples applying the methods to imaging data from human patients.

Example 1

Simulations

An arterial input function (AIF) was simulated using a gamma-variate function that has been shown in previous studies to correlate well with physiologically measured AIFs. See for example, the above-cited reference by Calamante et al. The analytical expression for the AIF was:

$$C_a(t) = \begin{cases} 0 & t \leq t_0 \\ C_o(t-t_0)^a e^{-(t-t_0)/b} & t > t_0 \end{cases} \quad [22]$$

with a=3.0 and b=1.5 s, representative of data from normal adult volunteers. Simulations used $C_o=1$, $t_0=20$ s over a time range of 200 s to avoid truncation for the longest MTT simulated (24 seconds).

To evaluate the techniques' sensitivity to different underlying R(t), three different models were examined: exponential, box-shaped, and linear. In all models, the mean transit time was calculated as MTT=CBV/CBF from the Central Volume Theorem. CBV was either 4% or 2%, values also used by other studies as representative for normal gray matter or white matter respectively. For CBV=4%, flow values were varied between 10-70 ml/100 g/min in 10 ml/100 g/min increments. For CBV=2%, flows were evaluated from 5 to 35 ml/100 g/min in 5 ml/100 g/min increments to maintain the same range of MTT values as for CBV=4%. Analytical expressions for C(t) were derived by convolving $C\alpha(t)$ with each R(t).

Signal curves were generated as $S(t)=S_0 e^{-kC(t)TE}$, with baseline MR image intensity, $S_0=100$ and TE=65 ms. For all simulations, the proportionality factor k was selected that resulted in a 40% peak signal drop at a flow rate of 60 m/100 g/min and CBV=4%, corresponding to values typically found in human gray matter. The signal enhancement curve for the AIF, $S_\alpha(t)$, was similarly modeled as S(t) except substituting $C_\alpha(t)$ for C(t). The proportionality constant, k, in this case, was selected to generate a peak signal drop of 60%, typically measured signal reductions for selected AIFs in our clinical PWI.

Using techniques described previously (Henkelman, Med. Phys., 12:232-233 (1985), noise was added to S(t) and $S_\alpha(t)$ to create signals with baseline SNR (signal-to-noise ratio) of 20 and 100. To evaluate the sensitivity of flow estimates to differences in tracer arrival times between the AIF and tissue signal, S(t) was shifted up to ±5 seconds with respect to $S_\alpha(t)$ in increments of 1 second, resulting in a total of 11 shifts. To simulate shifts that are not multiples of the sampling period, signals were created with Δt=100 ms, shifted after noise was added and then resampled to TR (sampling rate)=1 or 1.5 second. A TR=1 second was used primarily to avoid confounds due to shifts that are not multiples of TR. Simulations were repeated at a TR=1.5 seconds to investigate the effects of sampling interval on the algorithms' performance.

Image data sets were created resulting in a total of 1024 data points for each TR, SNR, shift, and flow. For sSVD (standard SVD) and cSVD (circulant SVD), $P_{SVD}$ was varied between 0 and 95%. For oSVD (circular deconvolution with minimization of the oscillation index), OI was varied between 0 and 0.5. To determine absolute flow values, the calculated CBF values were rescaled by the k-factors used above for S(t) and $S_\alpha(t)$.

The following steps were repeated for each SNR and TR. For each $P_{SVD}$ and OI, the error at each iteration t ($E_t$) was calculated as $E_t=1/N_f\Sigma|F-F'|$ where F is the true flow value, F' is the calculated flow value, and $N_f$ is the number of simulated flow values ($N_f=7$). The optimal $P_{SVD}$ for sSVD and cSVD and optimal OI for oSVD were determined as the values which minimized simultaneously over all assumed residue functions R(t) and $N_t=1024$ iterations the average $E_t$ assuming zero time delays. The optimal $P_{SVD}$ and OI thresholds found in this step were then used to assess the performance of the techniques in terms of its mean error $E_t(\bar{E}(D)=1/N_t\Sigma E_t)$ and standard deviation ($\sigma_\epsilon(D)$) over all $N_t=1024$ iterations, as a function of tracer arrival time differences (D).

Tracer arrival timing differences between tissue and the AIF were estimated as the sample point, m, where the maximum R(t) occurs. For sSVD, the estimated shift D'=m·TR. For oSVD, D'=m·TR for m<L/2 and D'=(L-m)·TR for L/2≤m<L, where L is the total number of points. The error in estimating tracer arrival time differences for each iteration t was calculated as $ED_t=1/N_f\Sigma|D-D'|$ where D is the true time difference, D' the estimated difference and $N_D$ is the number of simulated applied shifts ($N_D$=11). The $P_{SVD}$ and OI used for estimating flows at each SNR and TR were used to estimate timing shifts. The mean delay error $ED_t$( $\overline{ED}(F)=1/N_t\Sigma ED_t$) over all $N_t$=1024 iterations as well as the standard deviation ($\sigma_{ED}(F)$) were calculated at each flow rate, F.

The results of these simulations were as follows.

Figure 3A:
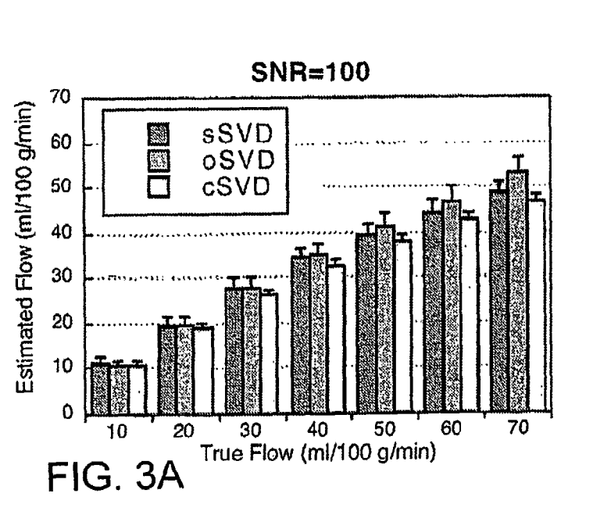
Figure 3B:
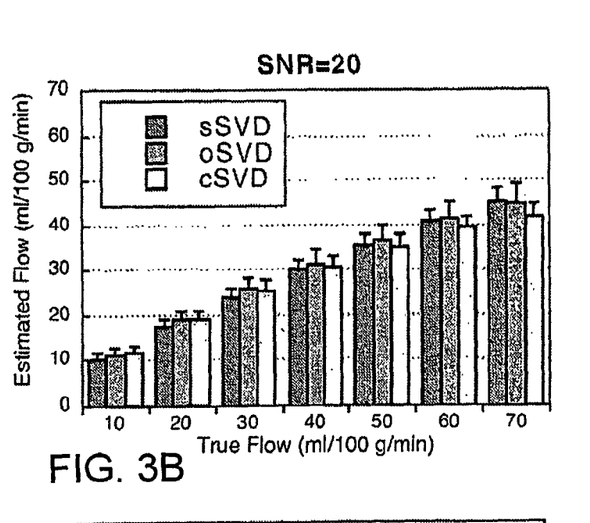

For TR=1 second and SNR=100 and 20, the optimal $P_{SVD}$ for sSVD were 4% and 20% respectively, for cSVD, they were 5% and 10%; and for oSVD, the optimal OI were 0.065 and 0.035. The performances of sSVD, oSVD, and cSVD in estimating flow assuming no phase shift between the AIF and C(t) were found to be comparable. As expected, greater underestimation of flow was found at low SNR compared to high SNR. FIGS. 3A-D show the results for TR=1 second, and CBV=4% and underlying monoexponential R(t) at SNR=100 (FIG. 3A) and SNR=20 (FIG. 3B). The three columns in each bar graph represent the sSVD (left, dark gray), oSVD (center, gray), and cSVD (right, very light gray), respectively.

Similar results were found for different R(t) (graphs not shown) except in the case of a box-shaped R(t) at SNR=100. In this condition, both sSVD and oSVD tended to overestimate high flows, while cSVD did not. In addition, for CBV=2% and SNR=20 (graphs not shown), cSVD performs slightly worse at low flow rates with greater overestimated flow, e.g., at 5 ml/100 g/min, cSVD estimated flow as 6.9±1.3 while sSVD overestimated flow as 6.1±1.2 and oSVD 5.5±1.1 ml/100 g/min.

Figure 3C:
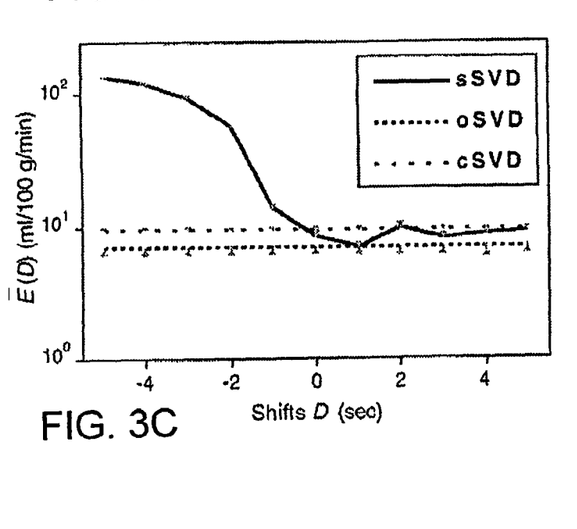
FIGS. 3C and 3D show $\overline{E}(D)$ and $\sigma_E(D)$ as a function of tracer arrival timing shifts (D) show sSVD's performance varies as a function of D while oSVD's and cSVD's performances do not.
Figure 3D:
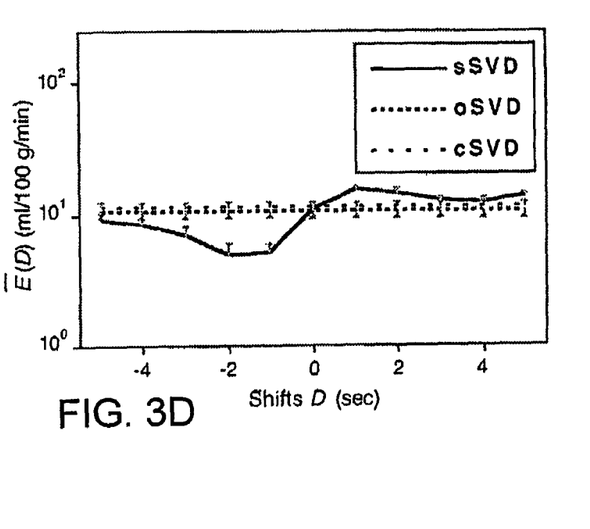

For all simulation conditions, $\overline{E}(D)$ for sSVD varied with timing shifts (D), especially when the AIF lags the tissue signal (D<0) as seen in FIGS. 3C and 3D. In contrast, both oSVD and cSVD are less sensitive to tracer arrival differences. At D=0, oSVD was found to perform comparably or better than sSVD (Table 1, below). However, the minimum $\overline{E}(D)$ for sSVD ($\overline{E}_{min}$) often did not occur at D=0 but depended on simulation conditions. For SNR=100, $\overline{E}_{min}$ occurred at D of +1, +1, +4 and +1 for monoexponential, linear, box-car R(t), and CBV=2% respectively. For SNR=20, $\overline{E}_{min}$ occurred at D of −2, −1, 0, and −1. For conspicuity in FIGS. 3C and 3D, only the upper error bars (1 SD) are shown for sSVD and cSVD and the lower error bars (1 SD) for oSVD.

Figure 4A:
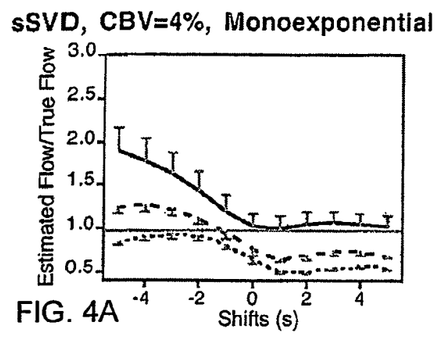
FIGS. 4A to 4F are a series of graphs showing a comparison of the three techniques' accuracy in estimating flow for different R(t) and MTTs (mean transit times). Shown are the ratios of F'/F as a function of shifts for MTT=24 seconds, 6 seconds, and 3.4 seconds, SNR=20, TR=1 second, and CBV=4% for sSVD and an R(t) that is (4A) monoexponential, (4B) linear, (4C) box-shaped, or (4D) monoexponential with CBV=2%. Results (4E) for oSVD and (4F) cSVD assuming monoexponential R(t) are also shown.
Figure 4B:
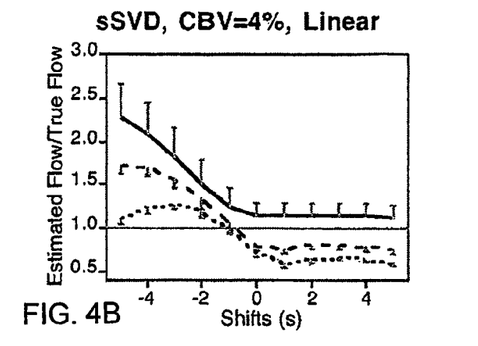
Figure 4C:
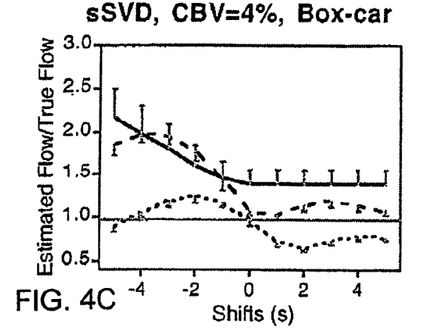
Figure 4D:
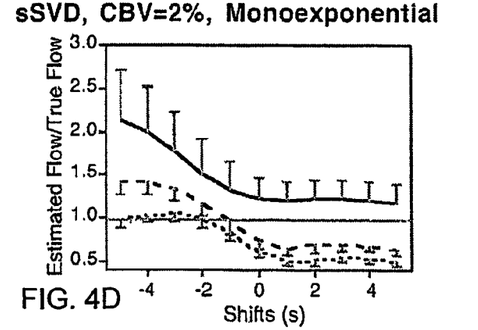
Figure 4E:
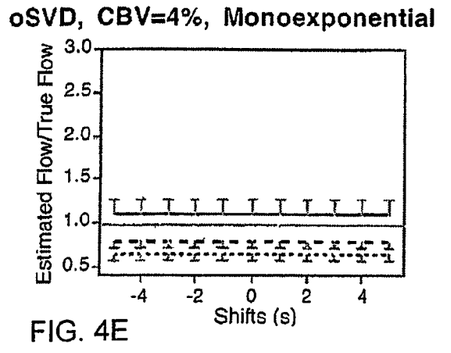
Figure 4F:
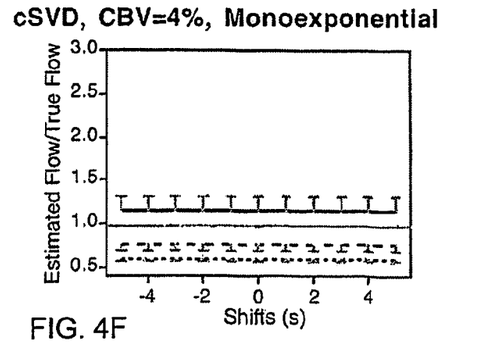

In contrast, the extent sSVD technique, which over- or underestimates flow, was found to depend on MTT, tracer timing shift, and R(t). On the other hand, the ratios of estimated flow (F') to true flow (F) for both oSVD and cSVD did not vary with shifts, but depended on MTT. This is illustrated in FIGS. 4A to 4F, which clearly demonstrate the variability of the magnitude of F'/F oscillations as functions of R(t) and MTT for sSVD. oSVD and cSVD produced results comprising of constant ratios as a function of tracer arrival differences independent of R(t). Graphs are shown for monoexponential R(t) (FIGS. 4E and 4F). For oSVD, the ratios also were independent of CBV, while cSVD performed less accurately at lower CBV and longer MTT (Table 2, below).

FIGS. 4A to 4F show a comparison of the three techniques' accuracy in estimating flow for different R(t) and MTTs. Shown are the ratios of F'/F as a function of shifts for SNR=20, TR=1 second, and CBV=4% for sSVD and an R(t) that is (4A) monoexponential, (4B) linear, (4C) box-shaped, or (4D) monoexponential with CBV=2%. Results (4E) for oSVD and (4F) cSVD assuming monoexponential R(t) are also shown. The upper error bar (1 SD) is shown for MTT=24 seconds (F=10 ml/100 g/min for CBV=4%; F=5 ml/100 g/min for CBV=2%) and lower error bars (1 SD) for MTT=6.0 seconds (F=40 ml/100 g/min for CBV=4%; F=20 ml/100 g/min for CBV=2%) and MTT=3.4 seconds (F=70 ml/100 g/min for CBV=4%; F=35 ml/100 g/min for CBV=2%).

TABLE 2

Mean ± SD of F'/F for MTT ranging from 3.4 to 24 seconds for oSVD and cSVD techniques assuming SNR = 20

| Simulation Condition | oSVD (ml/100 g/min) | cSVD (ml/100 g/min) |
|---|---|---|
| Monoexponential R(t) | .64 ± .06 to 1.10 ± .16 | .60 ± .04 to 1.15 ± .17 |
| Linear R(t) | .72 ± .06 to 1.14 ± .16 | .69 ± .05 to 1.25 ± .17 |
| Box-car R(t) | .95 ± .09 to 1.51 ± .21 | .87 ± .05 to 1.60 ± .22 |
| CBV = 2% | .56 ± .07 to 1.11 ± .23 | .56 ± .06 to 1.39 ± .25 |

Figures 5A, 5C:
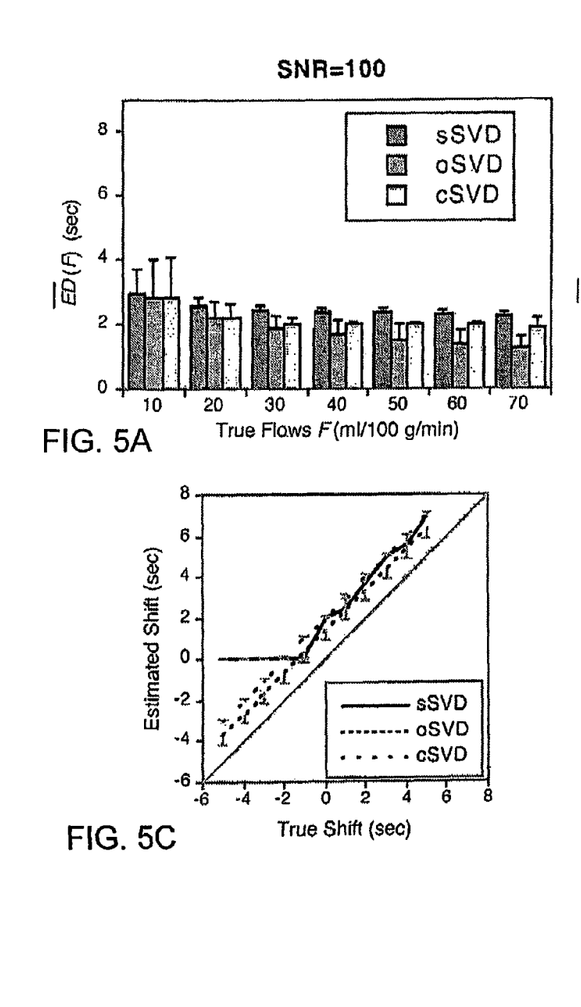
Figures 5B, 5D:
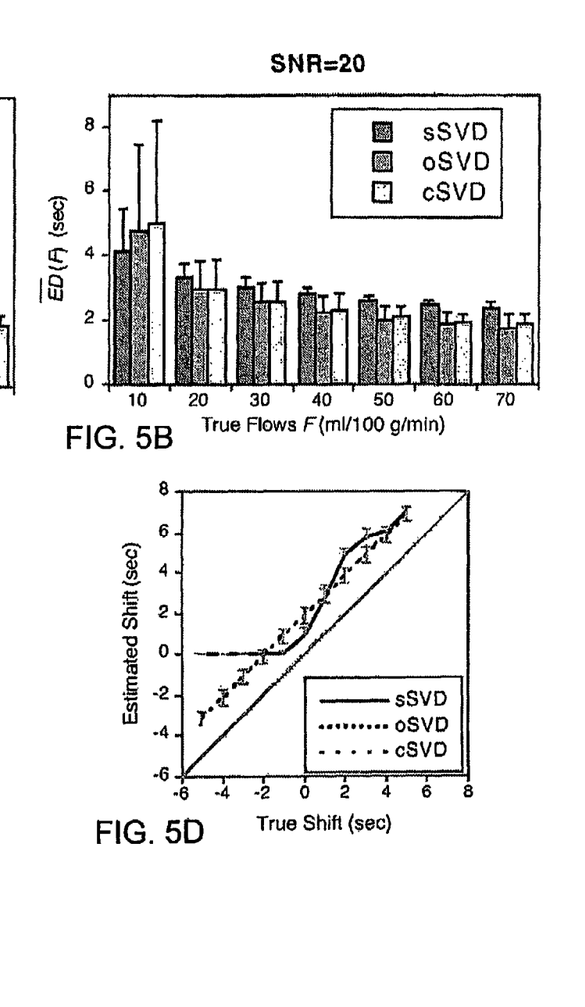

The effects of SNR and flow rate on the estimation of timing shifts are shown in FIGS. 5A-B. Low flow rates produce the worst estimates. At high flow rates, oSVD and cSVD have lower $\overline{ED}(F)$ than sSVD. However, at low flow rates at

TABLE 1

$\overline{E}(D) \pm \sigma_E(D)$ for D = 0 as well as $\overline{E}_{min}$ for sSVD compared to average $\overline{E}(D) \pm \sigma_E(D)$ of oSVD and cSVD for different SNRs, residue functions and blood volume (CBV = 4% vs CBV = 2%)

| | SNR = 100 | | | | SNR = 20 | | | |
|---|---|---|---|---|---|---|---|---|
| Simulation Condition | sSVD (D = 0) | sSVD ($\overline{E}_{min}$) | Osvd | cSVD | sSVD (D = 0) | sSVD ($\overline{E}_{min}$) | oSVD | cSVD |
| | | (ml/100 g/min) | | | | (ml/100 g/min) | | |
| Monoexponential R(t) | 8.42 ± .79 | 7.04 ± .60 | 7.03 ± .90 | 9.46 ± .47 | 11.10. ± .77 | 4.98 ± .96 | 10.56 ± 1.09 | 11.64 ± .85 |
| Linear R(t) | 4.19 ± .84 | 3.29 ± .53 | 3.64 ± .90 | 4.80 ± .53 | 9.03 ± .86 | 3.46 ± .95 | 8.15 ± 1.22 | 9.01 ± 1.04 |
| Box-car R(t) | 9.57 ± 1.02 | 6.56 ± .77 | 9.30 ± 1.45 | 6.28 ± .65 | 4.34 ± .90 | 4.34 ± .90 | 7.60 ± 1.42 | 7.17 ± 1.09 |
| CBV = 2% | 4.44 ± .61 | 3.43 ± .47 | 4.02 ± 0.51 | 4.71 ± .37 | 6.12 ± .70 | 3.06 ± .79 | 6.77 ± 0.73 | 6.73 ± .70 |

In summary, these results indicate that both model-independent techniques (OSVD and CSVD) are insensitive to tracer arrival time differences. Importantly, they also perform comparably to the standard SVD (sSVD) technique when there are no differences between tracer arrival time of the AIF and the tissue signal (FIGS. 3A-3D).

SNR=20, sSVD estimates have both lower $\overline{ED}(F)$ and $\sigma_{ED}(F)$ than oSVD and cSVD. Similar behavior was found for the other simulation conditions (graphs not shown). However, there is a systematic error in sSVD in estimating negative shifts at both high and low SNR, demonstrated in FIGS. 5C-D for the case F=601 ml/100 g/min. For positive delay values, sSVD performs comparably to oSVD and CSVD at high SNR. At SNR=20, sSVD is more accurate determining small shifts, but less accurate for large shifts compared to oSVD and cSVD. However, when the shift is negative, sSVD has a systematic bias since the technique inherently cannot distinguish negative time shifts from zero time shifts whereas both cSVD and oSVD can. Similar findings were obtained under other simulation conditions (graphs not shown).

FIGS. 5A-D show a comparison of performances of sSVD, oSVD, and cSVD in estimating tracer arrival time differences for SNR=100 (5A) and 20 (5B) with TR=1 second, and CBV=4% and underlying monoexponential R(t). $\overline{ED}(F)$ and $\sigma_{ED}(F)$ plotted as a function of F demonstrate that all techniques produce poor estimates at low flow. sSVD produces less $\overline{ED}(F)$ at low flow rates and SNR than oSVD and cSVD. FIGS. 5C and 5D show estimated shifts (D') as a function of true shift (D) at F=60 ml/100 g/min, and demonstrate that for D≧0, sSVD performs comparably to cSVD and oSVD at SNR=100, and overestimates large shifts to a greater extent at SNR=20. For D<0, sSVD has a systematic error, whereas both oSVD and cSVD do not. For conspicuity, upper error bars (1 SD) are shown for sSVD and cSVD and lower error bars (1 SD) are shown for oSVD.

Repeating the above simulations with TR=1.5 seconds produced results similar to that obtained with TR=1 second. For SNR=100 and 20, the optimal $P_{SVD}$ for sSVD were 4% and 10% respectively; and for cSVD, they were 3% and 10%; for oSVD, the optimal OI were 0.085 and 0.095. Greater underestimation of flow than at TR=1 second was found for all techniques at high flow rates at both SNRs. The same sensitivity to time shifts for sSVD flow estimates were detected, while oSVD and cSVD were still shift independent. However, oscillations in $\overline{E}(D)$ were detected for shifts that were not multiples of TR for oSVD and cSVD, albeit of smaller magnitude than that due to noise and compared to sSVD's oscillations. The accuracy of time shift estimates continued to have poorer estimates at low flow rates. In addition, time shift estimates were quantitized to units of 1.5 seconds for all three techniques since shifts that were not multiples of TR cannot be characterized in this present implementation.

In summary, these findings suggest that even in the absence of tracer arrival time differences sSVD CBF values are underestimated, making absolute quantification of CBF difficult. These results also show that if MTT is preserved, the accuracy of CBF estimates in gray and white matter would be comparable, e.g., estimates at CBV=4% and at CBV=2% (FIGS. 4A, 4D), producing ratios of gray to white matter CBF values that correlate well with those from other quantitative imaging modalities. This is consistent with findings from studies performed on normal human volunteers comparing MR CBF with PET and SPECT CBF values.

We also investigated the effects of changing sampling rate and their implications on flow determination. As the TR increases, the performances of all algorithms degrade for estimating high flow rates. This is almost surely due to insufficient temporal sampling to properly characterize the hemodynamic properties of the measured tissue. Furthermore, the optimal thresholds for sSVD, oSVD, and cSVD techniques also change, becoming less stringent, with more data points in W and $W_c$ kept. In the presence of arrival time differences that are not multiples of TR, oSVD and CSVD also exhibit slight oscillations. Although this is the most likely situation in clinically acquired data, the fluctuations that result are smaller in magnitude than those due to noise as well as being less than the fluctuations measured in sSVD. Furthermore, by interpolating the signal to higher sampling rates, one can potentially compensate for flow errors due to these non-sample-unit shifts.

Of the techniques investigated in this study that used block-circulant matrices, the oSVD technique, which varied the SVD threshold on an individual voxel basis, showed improved estimation over cSVD that had used a global SVD threshold. We did not separately compare improvements that may be due to voxel-based adaptive threshold techniques with those due to use of a block-circular matrix (cSVD), since sSVD did not include cSVD's robustness to AIF lags to the tissue signal. There may be alternate methods for adaptively minimizing oscillations based on each individual voxel's tissue signal characteristics than what has been proposed, which may further improve oSVD flow estimates.

Finally, the results also showed that at high flow rates, all techniques perform comparably (FIGS. 5A-D). At low flow rates, all techniques have larger errors. sSVD, however, cannot estimate negative shifts (FIGS. 5C-D) and therefore oDelay maps are preferable.

Example 2

Clinical MRI Acquisition

DSC MRI, as described in Example 1, consisted of spin-echo echo planar images obtained during the first pass of 0.2 mmol/kg of a gadolinium-based contrast agent injected 10 seconds after start of imaging at a rate of 5 ml/s using an MR imaging-compatible power injector (Medrad, Pittsburgh, Pa.). Imaging studies were performed on 1.5 T GE Signa LX systems (GE Medical Systems, Milwaukee, Wis.). TR/TE=1500/65 ms and a field of view of 22×22 cm$^2$ or 20×20 cm$^2$ with an acquisition matrix of 128×128. All studies consisted of 11 slices with a thickness of 6 mm and gap of 1 mm collected over 46 time points.

All data analysis was performed retrospectively. Four patients were retrospectively examined. Patient demographics are shown in Table 3, below. Based on the simulation results, our analysis was limited to sSVD and oSVD. Relative CBF (sCBF and oCBF) and Delay (sDelay and oDelay) maps were calculated using the same techniques as for the simulations. An AIF was selected from the ipsilateral hemisphere and used for analysis for both sSVD and oSVD. Selection of $P_{SVD}$ for SSVD and OI for oSVD were based on the optimal values found in the simulation section for SNR=20 and TR=1.5 seconds, typical for clinically acquired PWI at this institution. Relative cerebral blood volume (CBV) was calculated by numerically integrating the ΔR2(t) curves (e.g., as described in Rosen et al., Magn. Reson. Q., 5:263-281 (1989) and Weisskoff et al., Magn. Reson. Med., 31:610 (1994). MTT values were calculated as sMTT=CBV/sCBF and oMTT=CBV/oCBF.

TABLE 3

Patient demographics, diagnosis, and imaging times

| Patient | Age/Sex | Diagnosis | Initial PWI | Follow-up |
|---|---|---|---|---|
| 1 | 67/F | Transient ischemic attack due to left ICA stenosis | Two weeks | T2 same day as PWI |
| 2 | 56/F | Right MCA stroke | 4 hrs | 22-day FLAIR |
| 3 | 62/M | Left MCA stroke | 7 hrs | 4 month FLAIR |
| 4 | 52/F | Right MCA stroke and complete right ICA occlusion | 11 hrs | 6 day FLAIR |

TABLE 3-continued

Patient demographics, diagnosis, and imaging times

| Patient | Age/ Sex | Diagnosis | Initial PWI | Follow-up |
| --- | --- | --- | --- | --- |

From the results of the Monte Carlo simulations, we limited our clinical analysis to sSVD and oSVD. Based on the calculated optimal thresholds for SNR=20 and TR=1.5 seconds, $P_{SVD}$ of 10% was used for sSVD and OI=0.095 was used for oSVD perfusion analysis.

In the case of Patient 1 (FIGS. 6A-I), we found that sSVD overestimates the amount of tissue at risk of infarction (6B, 6C) while oSVD maps (6F, 6G) show much smaller regions of abnormalities although both sSVD and oSVD maps were created with the same AIF. Patient 1's initial DWI (FIG. 6A) and CBV (6E) show no abnormalities while the regions of abnormalities on sCBF and sMIT (6B, 6C) correspond with regions of the greatest phase shifts on the delay maps (6D, 6H). The abnormailities on oSVD maps correspond with chronic regions of hyperintensity on the patient's T2 fast spin echo (FSE) (I) acquired at the same session. The patient was diagnosed with TIA.

Figures 6A, 6E:
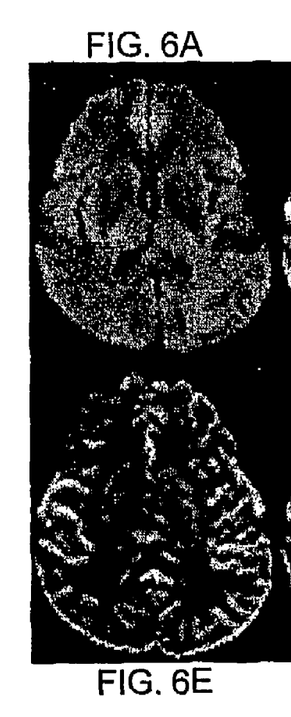
FIG. 6A shows a normal appearing DWI.
FIG. 6E shows a normal appearing CBV.
Figures 6B, 6C, 6F, 6G:
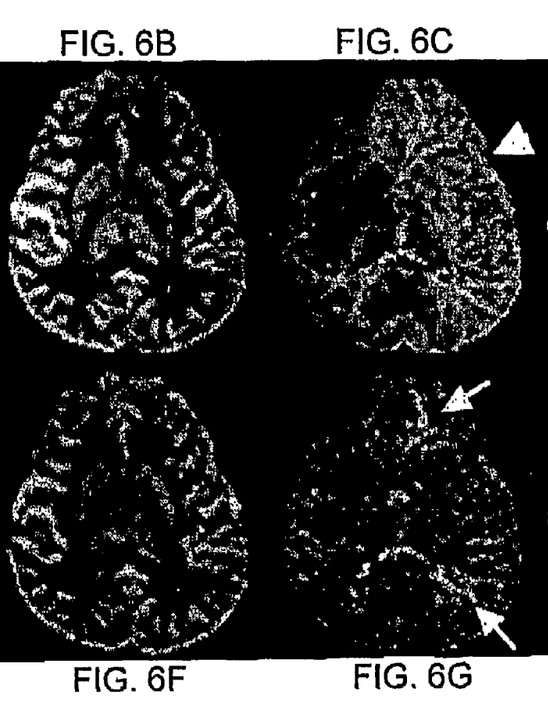
Figures 6D, 6H:
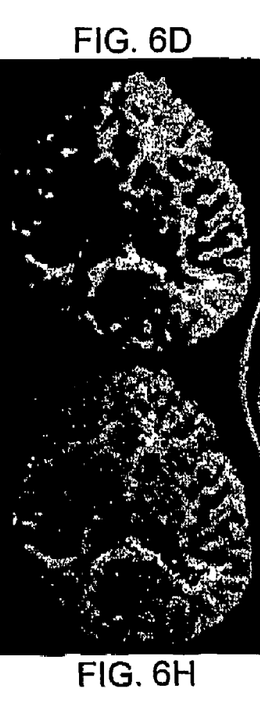
FIG. 6D shows an sDelay map.
FIG. 6H shows an oDelay map.
Figure 6I:
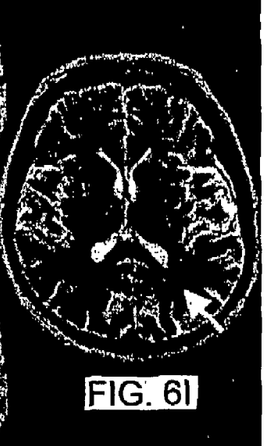
FIG. 6I shows the T2 FSE with chronic regions of hyperintensities.

In particular, FIGS. 6A to 6I show the performances of sSVD and oSVD techniques in a patient (Patient 1), who had an ICA stenosis in which there were large sCBF and sMTT abnormalities (arrowheads) that did not infarct and minimal oCBF and oMTT lesions (arrows). Imaging studies were acquired 2 weeks after episodes of transient right-sided weaknesses. FIG. 6A shows a normal appearing DWI. FIG. 6B shows the sCBF, FIG. 6C shows the sMTT (arrow), and FIG. 6D shows the sDelay map. FIG. 6E shows a normal appearing CBV, FIG. 6F shows the oCBF, FIG. 6G the oMTT (arrows), and FIG. 6H shows the oDelay map. FIG. 6I shows the T2 FSE with chronic regions of hyperintensities (arrow).

FIGS. 7A to 7I demonstrate that for Patient 2 sSVD and oSVD can both accurately identify tissue that ultimately infarcts on follow-up imaging (I) although presenting only with minimal initial DWI (7A) and CBV (7E) abnormalities. Large perfusion abnormalities are evident in both sSVD (7B, 7C) and oSVD (7F, 7G) maps and correspond with regions of large shifts on the delay maps for both techniques (7D, 7H). This demonstrates that oSVD, although more specific as demonstrated by FIGS. 6A-I can be still sensitive enough to detect tissue at risk of infarction that is initially normal appearing on CBV and DWI maps.

Figure 7A:
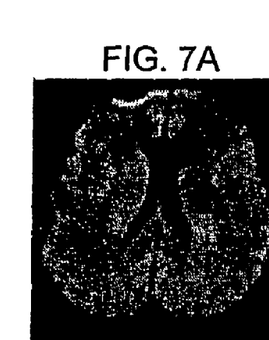
Figure 7B:
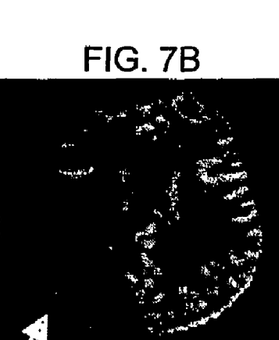
FIG. 7B shows the sCBF (perfusion map, see lesion at arrow)
Figure 7C:
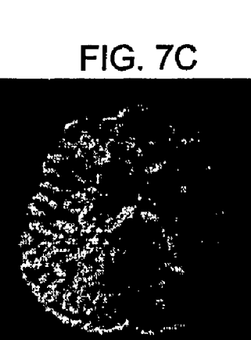
Figure 7D:
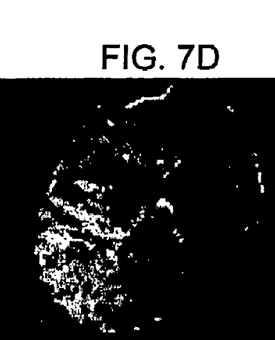
Figure 7E:
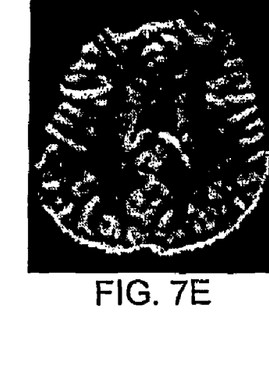
Figure 7F:
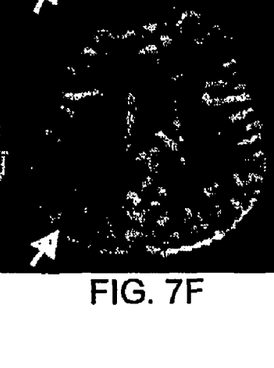
Figure 7G:
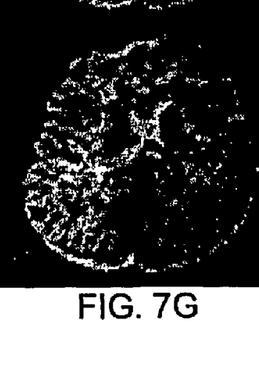
FIG. 7G shows the oMTT.
Figure 7H:
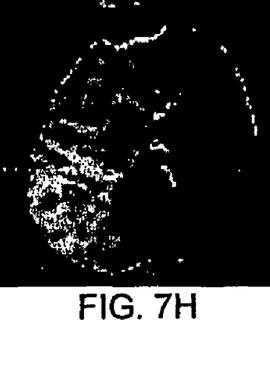
FIG. 7H shows the oDelay map.
Figure 7I:
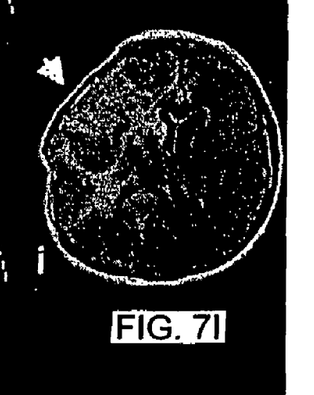

In particular, FIGS. 7A to 7I show that both sSVD and oSVD can detect regions of tissue at risk of infarction that is initially normal in the DWI. FIG. 7A shows a normal DWI. FIG. 7B shows the sCBF (perfusion map, see lesion at arrow), FIG. 7C shows sMTT, FIG. 7D the sDelay map, FIG. 7E the CBV, FIG. 7F the oCBF (arrow shows lesion), FIG. 7G shows the oMTT, and FIG. 7H shows the oDelay map. FIG. 7J shows a 22-day follow-up FLAIR, which shows the infarct lesion matches with abnormalities on both sSVD and OSVD perfusion maps (arrows).

FIGS. 8A to 8I demonstrate how OSVD can provide a more specific indicator of tissue at risk of infarction than sSVD by providing an example where there is mismatch in DWI and PWI lesion volumes using sSVD and no mismatch when using oSVD as in the case of Patient 3. The sSVD perfusion maps (8B, 8C) show a much larger volume of tissue at risk of infarction than the amount of tissue shown to have infarcted on the 4-month follow-up T2 FLAIR (8I). In contrast, the oSVD maps (8F, 8G) do not demonstrate a mismatch in lesion volumes with the DWI (8A) and CBV (8E), and correspond well with the follow-up lesion volume (8I).

Figure 8A:
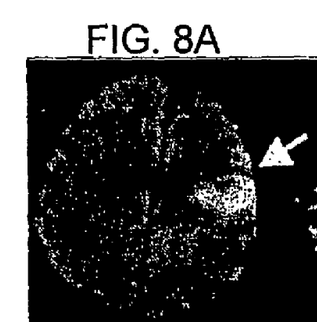
FIG. 8A shows a normal DWI.
Figure 8B:
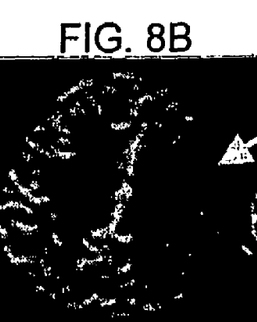
FIG. 8B shows the sCBF, FIG. 8C the sMTT.
Figure 8C:
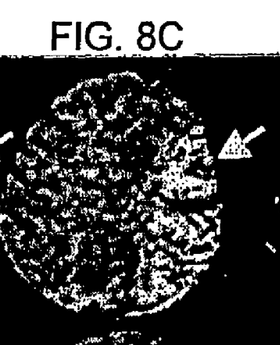
Figure 8D:
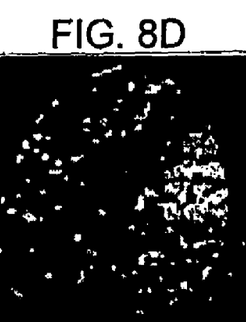
FIG. 8D shows the sDelay map.
Figure 8E:
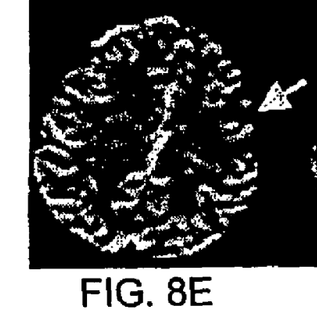
Figure 8F:
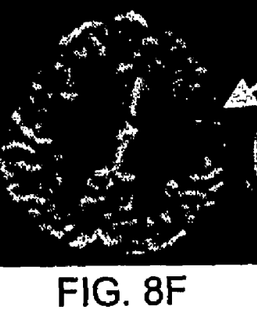
FIG. 8F shows oCBF.
Figure 8G:
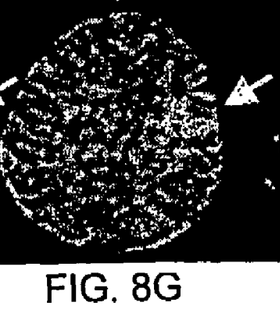
FIG. 8G shows oMTT.
Figure 8H:
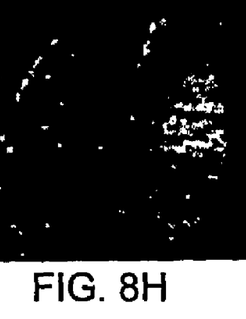
FIG. 8H shows an oDelay map.
Figure 8I:
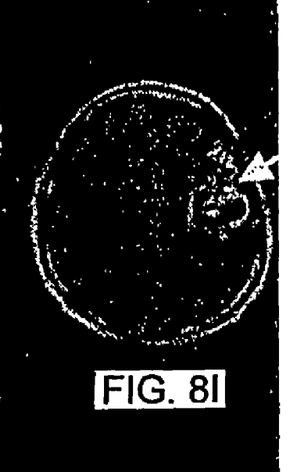

In particular, FIGS. 8A to 8I show a mismatch in DWI and PWI lesion volumes when using sSVD and no mismatch when using oSVD (arrows show lesion). FIG. 8A shows a normal DWI. FIG. 8B shows the sCBF, FIG. 8C the sMTT, FIG. 8D shows the sDelay map. FIG. 8E shows the CBV. FIG. 8F shows oCBF, FIG. 8G shows oMIT, and FIG. 8H shows an oDelay map. FIG. 8J shows a 4 month follow-up FLAIR, which shows an infarct that is well matched with the patient's acute DWI, CBV, oCBF, and oMTT studies (arrows).

Figure 9A:
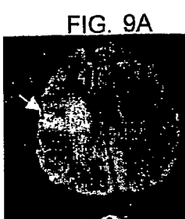
Figure 9B:
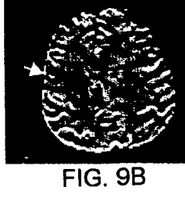
Figure 9C:
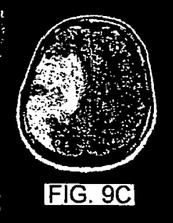

FIG. 9A to 9P demonstrate the sensitivity of both techniques to AIF selection in the case of Patient 4. An AIF selected from the ipsilateral hemisphere along the expected course of the MCA (AIF 1) results in sSVD perfusion maps (9B, 9C) that appear hypoperfused in regions that are inconsistent with the patient's initial DWI (9A), initial CBV (9B) and follow-up FLAIR study (9C). From the delay maps, we see that regions identified as hypoperfused by sCBF correspond to negative time differences on the oDelay maps (9I). In regions that appear hyperperfused (9D, arrows), AIF 1 slightly lags the tissue signal as indicated by the $\Delta R_2(t)$ curves for AIF 1 and ROI 2 (9J). The results of oSVD (9F, 9G), on the other hand, show regions of hypoperfusion that correspond well with the patient's DWI (9A) and CBV (9B) lesion, although they underestimate the amount of tissue that infarcts as identified on follow-up imaging (9C). The oDelay map (9I), however, shows regions with large positive delays that correspond well with the patient's follow-up lesion (9I).

Choosing instead an AIF from the patient's right posterior cerebral artery (AIF 2) results in sSVD maps (9K-9M) that are quite different from their counterparts using AIF 1 (9B-9D) and that correspond better with the patient's follow-up infarct volume (9C). oSVD maps, on the other hand, are comparable to those created with AIF 1 with the exception that the oDelay map in this case is positive. The relative sCBF ratio of ROI 1/ROI 2 was 401% for AIF 1 and 35% for AIF 2. For oSVD, the oCBF ratio of ROI 1/ROI 2 was 84% for AIF 1, and 88% for AIF 2.

Figure 9D:
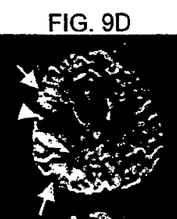
Figure 9E:
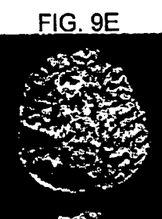
Figures 9F, 9I:
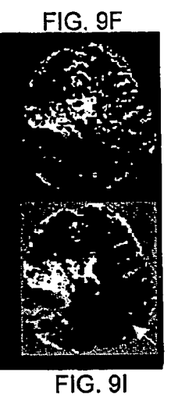
Figure 9G:
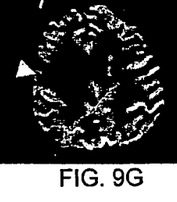
Figure 9H:
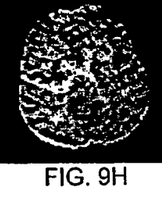
Figure 9J:
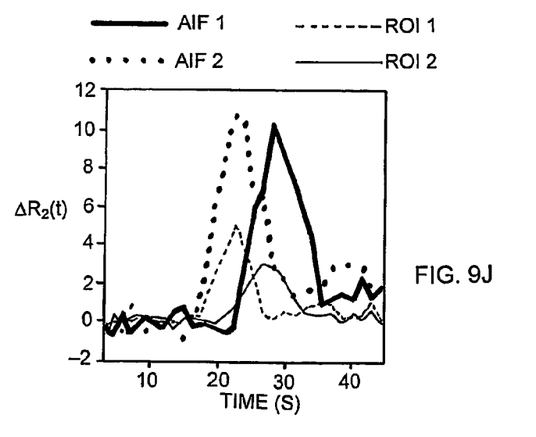
FIGS. 9J is a graph showing $\Delta R_2(t)$ for both AIFs and for two 5×5 ROIs.
Figure 9K:
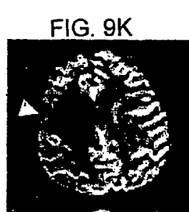
Figure 9L:
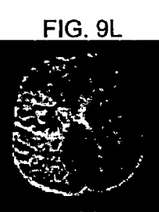
Figure 9M:
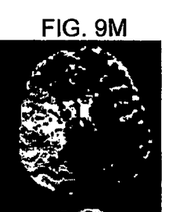
Figure 9N:
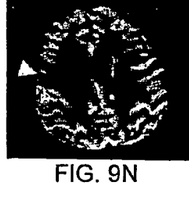
Figure 9O:
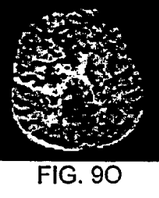
Figure 9P:
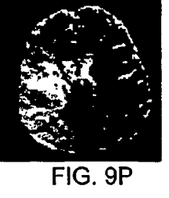

In particular, FIGS. 9A to 9P show a comparison of sensitivity of sSVD and oSVD to AIF selection in Patient 4. Lesions on initial (9A) DWI and (9B) CBV studies (small arrows) extend into larger infarct volume shown on (9C) 6-day follow-up FLAIR. FIGS. 9D (sCBF), 9E (sMTT), 9F (sDelay), 9G (oCBF), 9H (oMTT), and 9I (oDelay maps) were imaged using AIF1. Regions darker than background on the (9I) oDelay map represent negative values (small arrow). FIGS. 9J is a graph showing $\Delta R_2(t)$ for both AIFs and for two 5×5 ROIs. FIGS. 9K (sCBF), 9L (sMTT), 9M (sDelay), 9N (oCBF), 9O (oMTT), and 9P (oDelay map) were imaged using AIF2. Regions of hyperperfusion (arrows) or hypoperfusion (arrowheads) depend on AIF selection for sSVD, but not for oSVD as best seen in FIGS. 9G and 9N.

In summary, these results show how the errors demonstrated by Monte Carlo simulations may translate in clinically acquired PWI, and how the proposed oSVD technique can compensate for such errors. Furthermore, our findings suggest that sCBF and sMTT maps are weighted by delayed tracer arrival. In 3 out of 4 cases (FIGS. 6A-I to 8A-I), the regions identified as hypoperfused with sSVD (B, C) correspond with regions of greatest delay (D, H). In regions of mismatch between sSVD and oSVD in tissue that did not infarct (FIGS. 6A-I and 8A-I), the ratio of the flow with respect to the contralateral hemisphere was reduced by as much as 50% for phase shifts >2 seconds. This is consistent with our simulation results (FIGS. 4A-F), which showed that for time delays in this range, CBF in normal gray matter (F=60 ml/100 g/min) can be underestimated by as much as 50%, whereas tissue without tracer delay are estimated more accurately. This is most evident assuming a box-car residue function which has been reported to correlate well with acquired human PWI. When monitoring relative flow ratios in sSVD, one may erroneously detect an overall 50% reduction that could be due to tracer arrival differences. Although OSVD can also underestimate flow by close to 50% (as shown in FIGS. 4A-F and Table 2), it does so for tissue with and without tracer arrival differences. Therefore, when performing relative CBF analysis, assuming equivalent flow rates, the ratio of tissue with delayed to non-delayed tracer arrival will be close to unity, resulting in less relative differences between the hemispheres in the oSVD generated maps. Furthermore, oSVD's use of an adaptive local threshold may provide additional accuracy over sSVD for different tissue types.

Our findings also demonstrate that delay insensitive CBF estimates using oSVD may provide results that are not only robust to differences in tracer arrival times but also to AIF selection (FIGS. 9A-D). Thus, oSVD maps will be less sensitive to user variability in AIF selection and make automated AIF selection algorithms more feasible (e.g., as described in Alsop D, Wedmid A, Schlaug G., Defining a local input function for perfusion quantification with bolus contrast MRI (abstract), Proceedings of ISMRM Tenth Scientific Meeting, Honolulu, Hi., 2002).

With flow estimates less contaminated by tracer arrival time differences between the AIF and tissue signals, improved identification of salvageable tissue should be possible. Due to tracer arrival delay, the existing sSVD techniques tend to produce estimates of flow suggesting ischemia in regions that are actually oligemic or normally perfused. This in turn may contribute to the large sensitivity, but lack of specificity, in traditional sCBF and sMIT maps. However, one can argue that clinically what is desired is a sensitive indicator of tissue with disturbed hemodynamics and therefore delay contamination in sCBF and sMTT maps are clinically useful features.

The shift maps may represent tissue downstream from an occlusion or stenosis, but which may still receive sufficient flow at the time of imaging. The oCBF maps, on the other hand, represent the instantaneous flow at the acquisition time. Since CBF is a dynamic process, a single snapshot may not be a sensitive predictor of future infarction. Therefore, we speculate that the oDelay maps presented here can continue to provide sensitivity in identifying tissue with disturbed hemodynamics while the oCBF maps provide a more specific snapshot of the severity of ischemia in tissue at risk of infarction.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for producing, with a medical imaging system, an image that is indicative of a delay-compensated blood flow parameter in a tissue of interest in a subject, the steps comprising:

a) administering a contrast agent to the subject;
b) acquiring, with the medical imaging system, image data from the subject during a passage of the contrast agent through the tissue of interest;
c) reconstructing images from the acquired image data;
d) calculating an arterial input function (AIF) from the reconstructed images;
e) calculating a residue function, using the calculated AIF, by circular-deconvolution to substantially suppress a delay between the calculated AIF and the passage of the contrast agent; and
f) producing an image indicative of a delay-compensated blood flow parameter in the tissue of interest, using the calculated residue function.

2. The method as recited in claim 1, in which step e) is performed by utilizing a block-circulant matrix produced from the calculated AIF.

3. The method as recited in claim 2, in which step e) is performed by utilizing a singular value decomposition of the produced block-circulant matrix.

4. The method as recited in claim 1, in which step e) includes applying a selected threshold so that singular values are substantially suppressed during deconvolution.

5. The method as recited in claim 4, in which step e) is repeated a plurality of times and a different threshold is applied during each repetition.

6. The method as recited in claim 1, in which step e) includes minimizing an oscillation index that is indicative of noise present in the calculated residue function.

7. The method as recited in claim 6, in which the oscillation index has the form:

$$O = \frac{1}{L} \frac{1}{f_{max}} \left( \sum_{k=2}^{L-1} |f(k) - 2 2 f(k-1) + f(k+2)| \right);$$

wherein:
O is the oscillation index;
L is a number of sample points;
$f$ is an estimated residue function;
$f_{max}$ is a maximum amplitude of $f$; and
k is an index indicative of a data point in $f$.

8. The method as recited in claim 6, in which step e) is repeated a plurality of times to calculate a plurality of residue functions and a different oscillation index is minimized for each residue function.

9. The method as recited in claim 1, in which the delay-compensated blood flow parameter is at least one of cerebral blood volume (CBV), cerebral blood flow (CBF), relative cerebral blood volume (rCBV), relative cerebral blood flow (rCBF), and mean transit time (MTT).

10. The method as recited in claim 1, in which the medical imaging system is at least one of a magnetic resonance imaging (MRI) system, a computed tomography (CT) imaging system, and a positron emission tomography (PET) system.

11. The method as recited in claim 1, in which the contrast agent is at least one of a paramagnetic contrast agent, a dye, and a bolus of oxygen.

12. The method as recited in claim 1, in which the AIF is calculated by averaging signal changes in pixels selected from a region of interest.

13. The method as recited in claim 12, in which the region of interest includes a large blood vessel.

14. The method as recited in claim 1, in which the tissue of interest is brain tissue.

* * * * *